(12) United States Patent
Smith

(10) Patent No.: US 9,314,233 B2
(45) Date of Patent: *Apr. 19, 2016

(54) SURGICAL ACCESS ASSEMBLY WITH SLEEVE AND ADJUSTABLE FASTENER

(71) Applicant: Covidien LP, Mansfield, MA (US)

(72) Inventor: Robert C. Smith, Middletown, CT (US)

(73) Assignee: Covidien LP, Mansfield, MA (US)

( * ) Notice: Subject to any disclaimer, the term of this patent is extended or adjusted under 35 U.S.C. 154(b) by 40 days.

This patent is subject to a terminal disclaimer.

(21) Appl. No.: 14/162,938

(22) Filed: Jan. 24, 2014

(65) Prior Publication Data

US 2014/0142392 A1    May 22, 2014

Related U.S. Application Data

(63) Continuation of application No. 13/415,971, filed on Mar. 9, 2012, now Pat. No. 8,668,641.

(60) Provisional application No. 61/469,247, filed on Mar. 30, 2011.

(51) Int. Cl.
*A61B 17/02* (2006.01)
*A61B 17/34* (2006.01)

(52) U.S. Cl.
CPC ......... *A61B 17/0293* (2013.01); *A61B 17/0218* (2013.01); *A61B 17/3423* (2013.01); *A61B 17/3431* (2013.01); *A61B 2017/347* (2013.01);
(Continued)

(58) Field of Classification Search
CPC ........... A61B 17/3423; A61B 17/0293; A61B 17/0218; A61B 17/3431; A61B 2017/3435; A61B 2017/3466; A61B 2017/347; A61B 2017/3429

USPC .................................................. 600/201–208
See application file for complete search history.

(56) References Cited

U.S. PATENT DOCUMENTS

| | | |
|---|---|---|
| 5,524,644 A | 6/1996 | Crook |
| 5,672,168 A | 9/1997 | de la Torre et al. |

(Continued)

FOREIGN PATENT DOCUMENTS

| | | |
|---|---|---|
| WO | WO 2004/030547 A1 | 4/2004 |
| WO | WO 2004/075741 A2 | 9/2004 |

(Continued)

OTHER PUBLICATIONS

European Search Report for corresponding EP12160681 mailing date Jul. 7, 2012.

*Primary Examiner* — Pedro Philogene

(57) ABSTRACT

A surgical access assembly and method of use is disclosed, including an access member, a tissue engaging member, a sleeve extending from a portion of the membrane, and a fastening member to couple the access member and the sleeve. The access member includes proximal and distal ends, at least one lumen disposed therethrough, and defines a longitudinal axis. The tissue engaging member includes a membrane having proximal and distal ends with opposing openings, and a passage therethrough for receiving the access member. A length of the tissue engaging member may be selectively adjustable by a user so as to provide a retraction force. The sleeve extends proximally from a portion of the membrane. The sleeve has a proximal end and a distal end with opposing openings, the distal end of the sleeve defined by a portion of the membrane. A fastening member couples the access member and the sleeve.

15 Claims, 14 Drawing Sheets

(52) U.S. Cl.
CPC . *A61B 2017/3429* (2013.01); *A61B 2017/3435* (2013.01); *A61B 2017/3466* (2013.01)

(56) References Cited

U.S. PATENT DOCUMENTS

| | | |
|---|---|---|
| 5,813,409 A | 9/1998 | Leahy et al. |
| 5,899,208 A | 5/1999 | Bonadio |
| 5,906,577 A | 5/1999 | Beane et al. |
| 6,033,428 A | 3/2000 | Sardella |
| 6,077,288 A | 6/2000 | Shimomura et al. |
| 6,382,211 B1 | 5/2002 | Crook |
| 6,578,577 B2 | 6/2003 | Bonadio et al. |
| 6,589,167 B1 | 7/2003 | Shimomura et al. |
| 6,623,426 B2 | 9/2003 | Bonadio et al. |
| 7,033,319 B2 | 4/2006 | Pulford et al. |
| 7,195,590 B2 | 3/2007 | Butler et al. |
| 7,238,154 B2 | 7/2007 | Ewers et al. |
| 7,650,887 B2 | 1/2010 | Nguyen et al. |
| 7,704,207 B2 | 4/2010 | Albrecht et al. |
| 7,727,146 B2 | 6/2010 | Albrecht et al. |
| 7,749,161 B2 * | 7/2010 | Beckman et al. ............. 600/208 |
| 7,909,760 B2 | 3/2011 | Albrecht et al. |
| 7,998,068 B2 * | 8/2011 | Bonadio et al. ............. 600/208 |
| 8,317,691 B2 * | 11/2012 | Bonadio et al. ............. 600/208 |
| 8,668,641 B2 * | 3/2014 | Smith ................ A61B 17/3423 600/203 |
| 2001/0037053 A1 | 11/2001 | Bonadio et al. |
| 2004/0267096 A1 | 12/2004 | Caldwell et al. |
| 2005/0020884 A1 | 1/2005 | Hart et al. |
| 2005/0090717 A1 | 4/2005 | Bonadio |
| 2005/0192483 A1 | 9/2005 | Bonadio et al. |
| 2005/0203346 A1 | 9/2005 | Bonadio et al. |
| 2006/0161050 A1 | 7/2006 | Butler et al. |
| 2006/0247498 A1 | 11/2006 | Bonadio |
| 2006/0247499 A1 | 11/2006 | Butler et al. |
| 2006/0247500 A1 | 11/2006 | Voegele et al. |
| 2006/0247678 A1 | 11/2006 | Weisenburgh, II et al. |
| 2007/0093695 A1 | 4/2007 | Bonadio et al. |
| 2007/0151566 A1 | 7/2007 | Kahle et al. |
| 2008/0281161 A1 | 11/2008 | Albrecht |
| 2010/0113883 A1 | 5/2010 | Widenhouse et al. |
| 2011/0021877 A1 | 1/2011 | Fortier et al. |
| 2011/0054258 A1 | 3/2011 | O'Keefe et al. |

FOREIGN PATENT DOCUMENTS

| | | | |
|---|---|---|---|
| WO | WO 2009/062548 | 5/2009 | |
| WO | WO2009/062548 | * 5/2009 | ................ 600/208 |

* cited by examiner

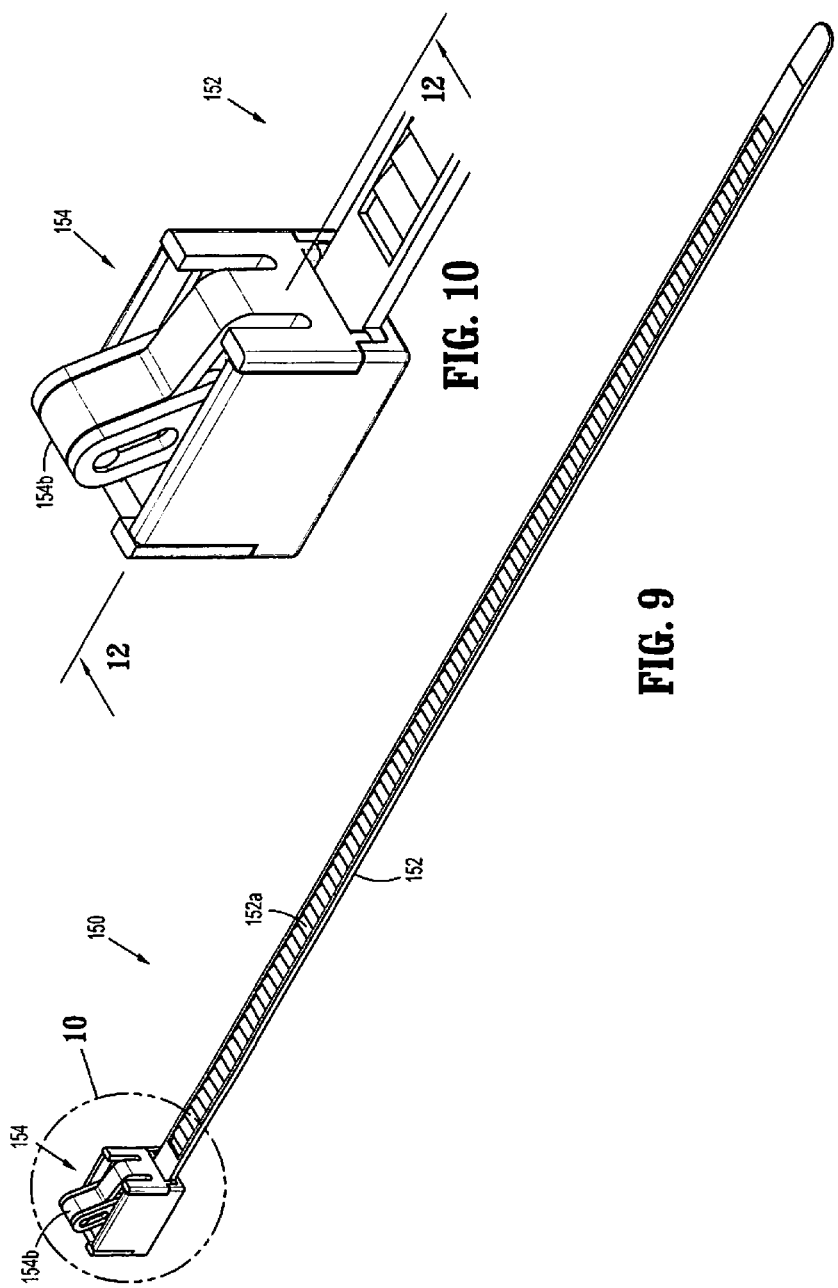

SURGICAL ACCESS ASSEMBLY WITH SLEEVE AND ADJUSTABLE FASTENER

CROSS-REFERENCE TO RELATED APPLICATIONS

This application is a continuation of U.S. patent application Ser. No. 13/415,971, filed Mar. 9, 2012, which claims priority to, and the benefit of, U.S. Provisional Patent Application Ser. No. 61/469,247, filed on Mar. 30, 2011, the entire contents of each of these prior applications are incorporated by reference herein.

BACKGROUND

1. Technical Field

The present disclosure relates to an access assembly for use in minimally invasive surgical procedures, such as endoscopic or laparoscopic-type procedures, and more particularly to an access assembly with an access member, a tissue engaging member, a sleeve, and a fastening member to couple the access member to the sleeve.

2. Background of Related Art

Today, many surgical procedures are performed through small incisions in the skin, as compared to the larger incisions typically required in traditional procedures, in an effort to reduce both trauma to the patient and recovery time. Generally, such procedures are referred to as endoscopic, unless performed on the patient's abdomen, in which case the procedure is referred to as laparoscopic. Throughout the present disclosure, the term minimally invasive should be understood to encompass both endoscopic and laparoscopic procedures. During a typical minimally invasive procedure, surgical objects, such as surgical access members (e.g., trocar and/or cannula assemblies), endoscopes, or other instruments, are inserted into the patient's body through the incision in tissue. Prior to the introduction of the surgical object into the patient's body, insufflation gases may be used to enlarge the area surrounding the target surgical site to create a larger, more accessible work area. Accordingly, the maintenance of a substantially fluid-tight seal is desirable so as to minimize the escape of insufflation gases and the deflation or collapse of the enlarged surgical site.

To this end, various access members are used during the course of minimally invasive procedures and are widely known in the art. A continuing need exists for access members that can be inserted into a variety of tissue incision sites and be secured in place to maintain the conditions of the insufflated surgical site. It is further desirable to accommodate a variety of tissue incisions and body surface conditions, and adapt to changing conditions at the surgery site, all while protecting the tissue surrounding a surgical site from damage.

SUMMARY

In accordance with various embodiments, the present disclosure is directed toward a surgical access assembly with an access member, a tissue engaging member, a sleeve to receive the access member, and a fastening member to couple the access member and sleeve.

The access member has a generally hourglass profile with proximal and distal ends, at least one lumen extending therethrough, and defines a longitudinal axis. The proximal and distal ends of the access member may include flanges to aid in securing the access member in a layer of tissue.

The tissue engaging member is disposed around the perimeter of a surgical site. The tissue engaging member includes a membrane having a proximal end and a distal end. The proximal and distal ends of the membrane engage a body surface and an internal tissue wall, respectively. The proximal end of the membrane is defined by a resilient ring having an arcuate or kidney bean shaped profile. A length of the tissue engaging member may be selectively adjustable by a user so as to provide a retraction force, e.g., so as to retract an incision.

Attached to, and extending around, an outer circumference of the distal ring is a sleeve that extends proximally through a passage defined by the tissue engaging member. The sleeve has opposing openings and a passage therethrough for receiving the access member. The sleeve forms a substantially fluid-tight seal with the access member. The sleeve is configured to move relative to the tissue engaging member. The sleeve may thus be inserted into the tissue engaging member with the access member disposed therein. In alternative embodiments, the sleeve may be attached to a portion of the distal ring, or may be attached to the ring itself. The sleeve may contain a protruding pocket on its outer circumference that receives a fastening member.

The fastening member circumferentially engages and couples the access member and the sleeve. The fastening member may be tightened around the access member and sleeve to provide a more secure coupling. The fastening member may be a band having a grooved surface, and further including a receiving member to receive the grooved surface after the fastening member is disposed around the sleeve and access member. The receiving member may further include a pawl to avoid undesired backing out of the band from the receiving member. In embodiments, the fastening member may be a band having spaced protrusions along its length, with a receiving member having an aperture or channel to securely receive the spaced protrusions. In other embodiments, the fastening member may be formed of separable members, each having a protrusion connected to a second protrusion having an aperture.

Also disclosed is a method of placing the surgical access assembly in a layer of tissue. An operator will dispose the proximal ring and the proximal end of the membrane proximally above the distal end of the membrane, and insert the distal ring into place at the distal end of the membrane. The operator will then insert the tissue engaging member into a tissue site and extend the sleeve above a body surface. The tissue engaging member may be rolled about the proximal end of the membrane to shorten its length. Rolling the proximal end of the membrane about the proximal ring also shortens the length of the sleeve to a desired length. Alternatively, an excess length of the sleeve may be removed by the operator. The operator then inserts an access member into the sleeve extending proximally from a portion of the membrane. The access member is then securely coupled to the sleeve through the use of an adjustable fastening member. The operator inserts the fastening member into a pocket formed on the outer circumference of the sleeve and adjusts the fastening member such that a desired compressive force is produced thereby forming a substantially fluid-tight seal.

Once the access member and the sleeve are securely coupled, the sleeve and access member are inserted into the tissue engaging member. Alternatively, the access member, sleeve, and tissue engaging member may be inserted into a layer of tissue in conjunction with each other. Excess sleeve material extending proximally above the access member and may be removed prior to use of the surgical access assembly. Surgical instruments may then be inserted through the access member and minimally invasive procedures can be performed.

The various aspects of this disclosure will be more readily understood from the following detailed description when read in conjunction with the appended drawings.

BRIEF DESCRIPTION OF THE DRAWINGS

Various exemplary embodiments of the present disclosure are described herein below with reference to the drawings, wherein:

FIG. 9 is a side perspective view of a fastening member having a band and a receiving member;

FIG. 10 is an enlarged detail view of the receiving member and a portion of the band;

DETAILED DESCRIPTION OF EMBODIMENTS

Figure 1:
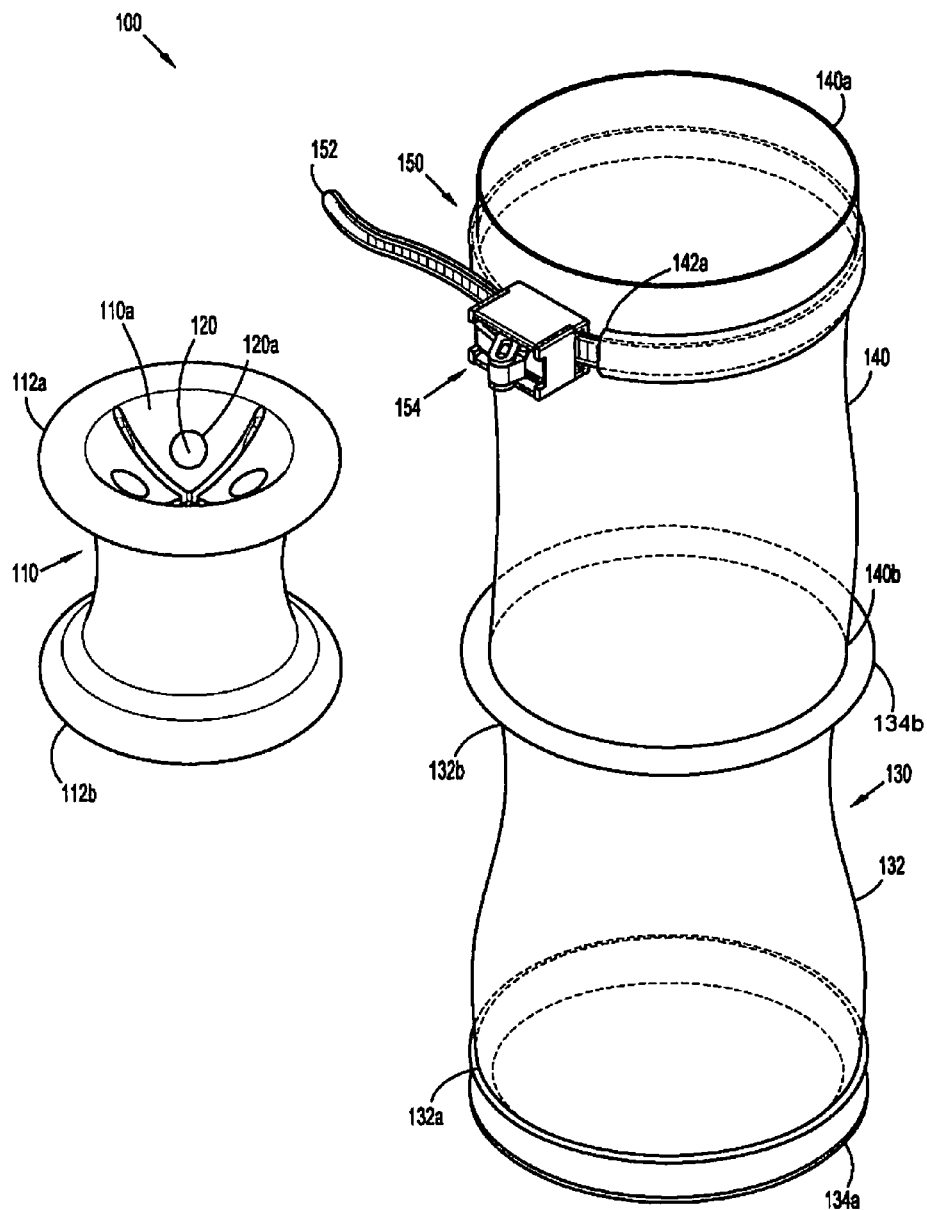
FIG. 1 is a side perspective view of the components of a surgical access assembly, including an access member, a tissue engaging member, a sleeve, and a fastening member.

The present disclosure will now describe in detail embodiments of a surgical access assembly with reference to the drawings in which like reference numerals designate identical or substantially similar parts in each view. Throughout the description, the term "proximal" will refer to the portion of the assembly closest to the operator, whereas the term "distal" will refer to the portion of the assembly farthest from the operator. Although discussed in terms of an incision for a minimally invasive procedure, the presently disclosed surgical access assembly may be used in any naturally occurring orifice (e.g. mouth, anus, or vagina).

Figure 8:
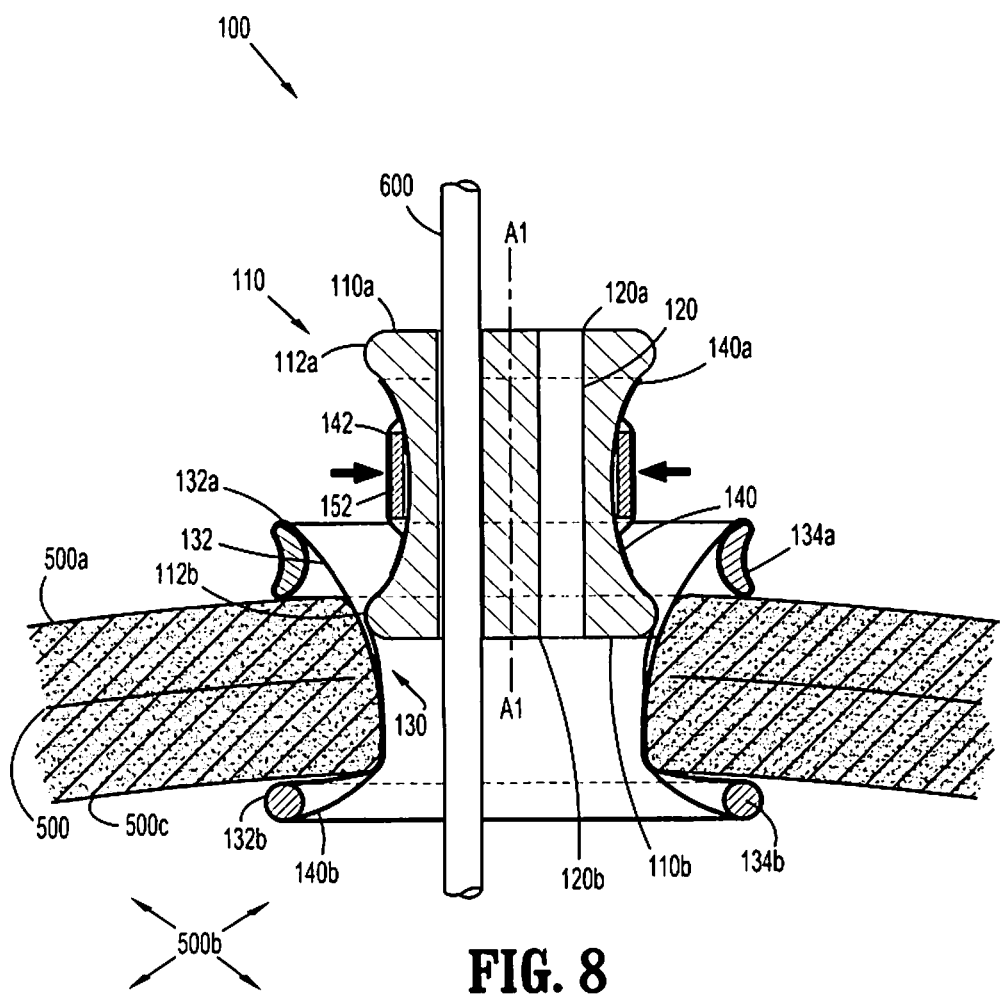
FIG. 8 is a side cross-sectional view of the surgical access assembly as shown in FIG. 7 as a surgical access member with a surgical instrument disposed therethrough is inserted into the sleeve.

Referring initially to FIG. 1, the components of a surgical access assembly 100 are shown prior to assembly. The surgical access assembly 100 includes an access member 110 having a generally hourglass shape, a proximal end 110a and a distal end 110b (FIG. 8), and defines a longitudinal axis A1 (FIG. 8). The proximal end 110a and the distal end 110b of the access member 110 are substantially perpendicular to the longitudinal axis A1. A flange 112a defines the proximal end 110a of the access member 110 and a flange 112b defines the distal end 110b of the surgical access member 110. The flanges 112a,b may serve to anchor the surgical access assembly 100 into a layer of tissue 500 (FIG. 5) or to another object. Access member 110 may be formed of a compressible element suitable for contact with internal body surfaces, such as foam.

Extending through the access member 110 along the longitudinal axis A1 is at least one lumen 120, and in embodiments, multiple lumens 120. The lumens 120 have entrance apertures 120a and exit apertures 120b (FIG. 8) disposed in the proximal end 110a and distal end 110b of the access member 110, respectively. The lumens 120 are disposed substantially parallel to the longitudinal axis A1. Lumens 120 provide a path for objects such as surgical instruments 600 (FIG. 8) to be inserted through the surgical access assembly 100. Lumens 120 may also provide a path for insufflation fluids to be introduced to an internal body cavity 500b (FIG. 5) below a layer of tissue 500. An access member of the type generally described above is disclosed in U.S. Patent Application Publication Nos. 2009/0093752 A1 and 2010/0240960 A1, the entire disclosures of which are incorporated by reference herein.

Figure 4:
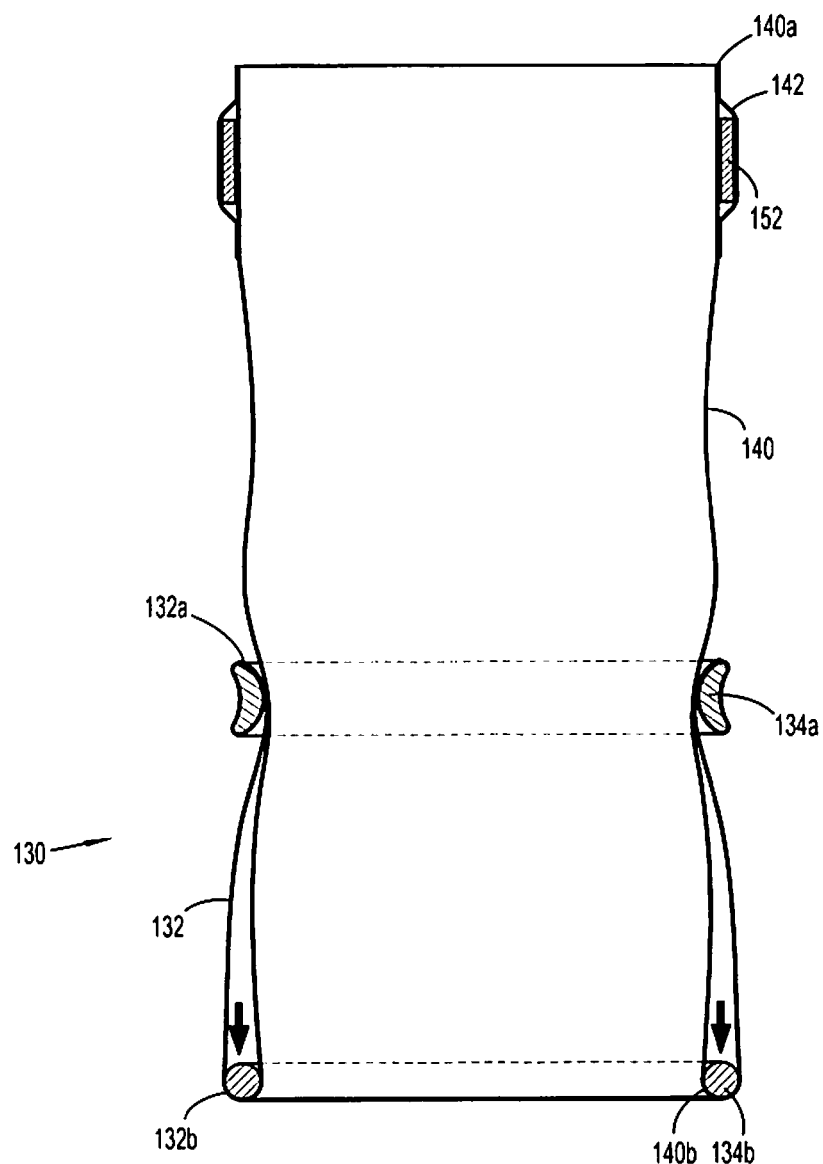
FIG. 4 is a cross-sectional view of the surgical access assembly as shown in FIG. 3 taken along section line 4-4.
Figure 5:
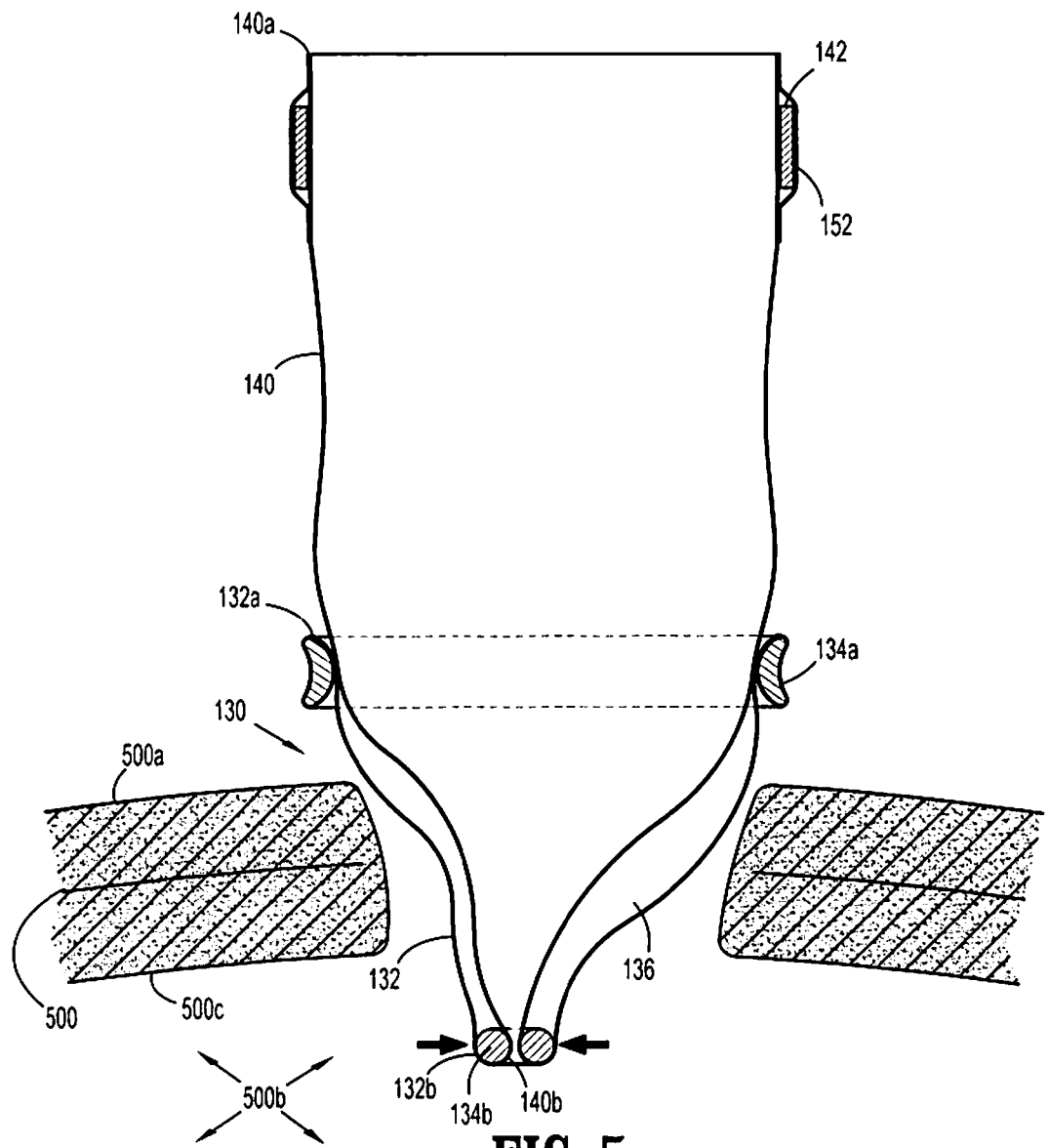
FIG. 5 is a side cross-sectional view of the surgical access assembly as shown in FIG. 4 as it is inserted into a layer of tissue.

Referring for the moment to FIG. 4, a tissue engaging member 130 includes a membrane 132 having a proximal end 132a and a distal end 132b. Tissue engaging member 130 is configured to be disposed around the perimeter of a layer of tissue 500 that defines a surgical site. Tissue engaging member 130 covers a portion of a body surface 500a (FIG. 5), extends into a tissue layer 500, and onto an internal tissue wall 500c (FIG. 5). Distal end 132b of membrane 132 contains a ring 134b that contacts an internal tissue wall 500c upon insertion into a layer of tissue 500. The ring 134b at the distal end 132b of membrane 132 is a resilient element over which membrane 132 is disposed. Proximal end 132a of membrane 132 is also defined by a ring 134a and contacts body surface 500a. Ring 134a is generally a resilient member having an arcuate or kidney bean shaped profile. Other cross-sectional profiles are contemplated for the resilient ring at the proximal end 132a of the membrane 132. The ring 134a and proximal end 132a of the membrane 132 are generally attached such that the ring 134a is not separable from the proximal end 132a of the membrane 132. Such attachment may be accomplished by, for example, stitching or fusion by heating.

Tissue engaging member 130 protects tissue layer 500 from damage caused by frictional engagement, shifting during operation, or other harmful forces caused during minimally invasive procedures. As such, tissue engaging member 130 is formed of a material suitable for prolonged contact with internal body surfaces.

The membrane 132 is disposed over the outer surface of the ring 134b at the distal end 132b of the membrane 132, extends proximally through the passage defined by the tissue engaging member 130 and defines a sleeve 140. Sleeve 140 extends proximally from the tissue engaging member 130, and has a proximal end 140a and a distal end 140b. Thus, the distal end 132b of membrane 132 is defined by the outside circumference of ring 134b, and the distal end 140b of sleeve 140 is defined by the inner circumference of ring 134b. Proximal and distal ends 140a, b of the sleeve 140 define opposing openings and a passage through the sleeve 140 that is configured to receive the access member 110.

Figure 19:
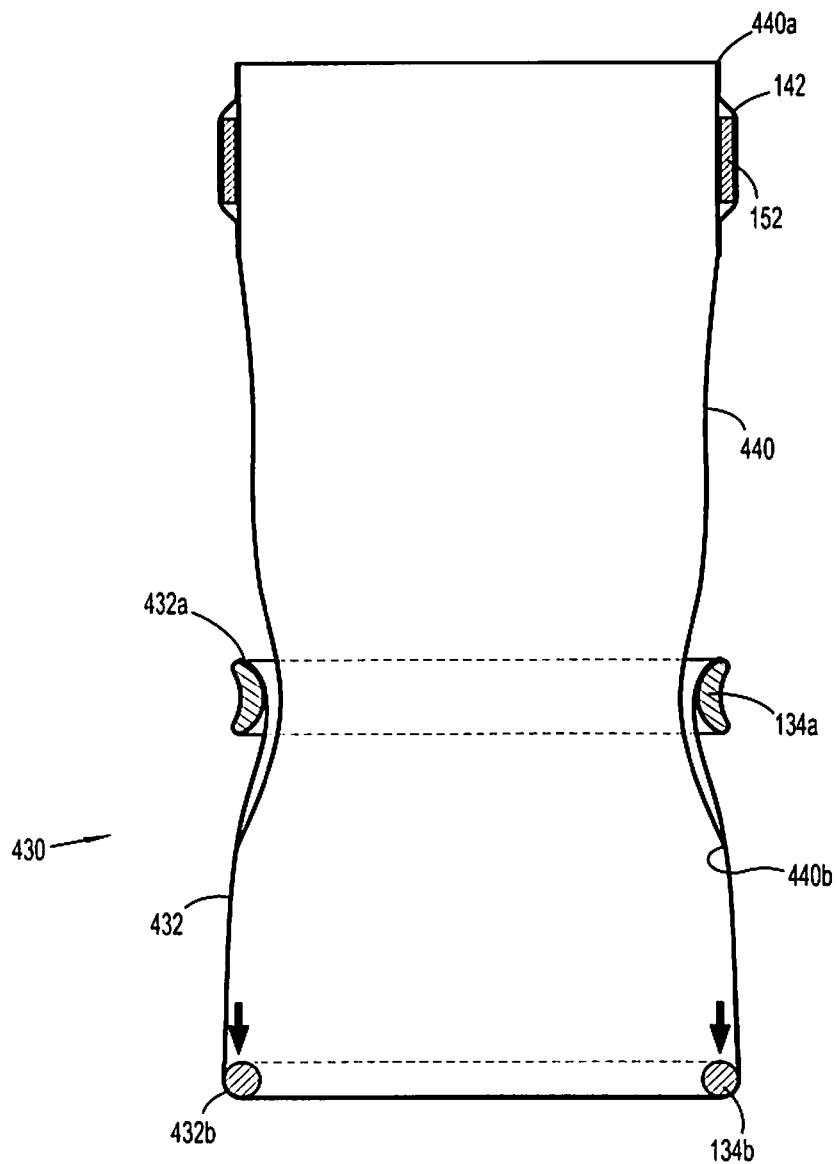
FIG. 19 is an embodiment of a sleeve with a distal end attached to a portion of a tissue engaging member.
Figure 20:
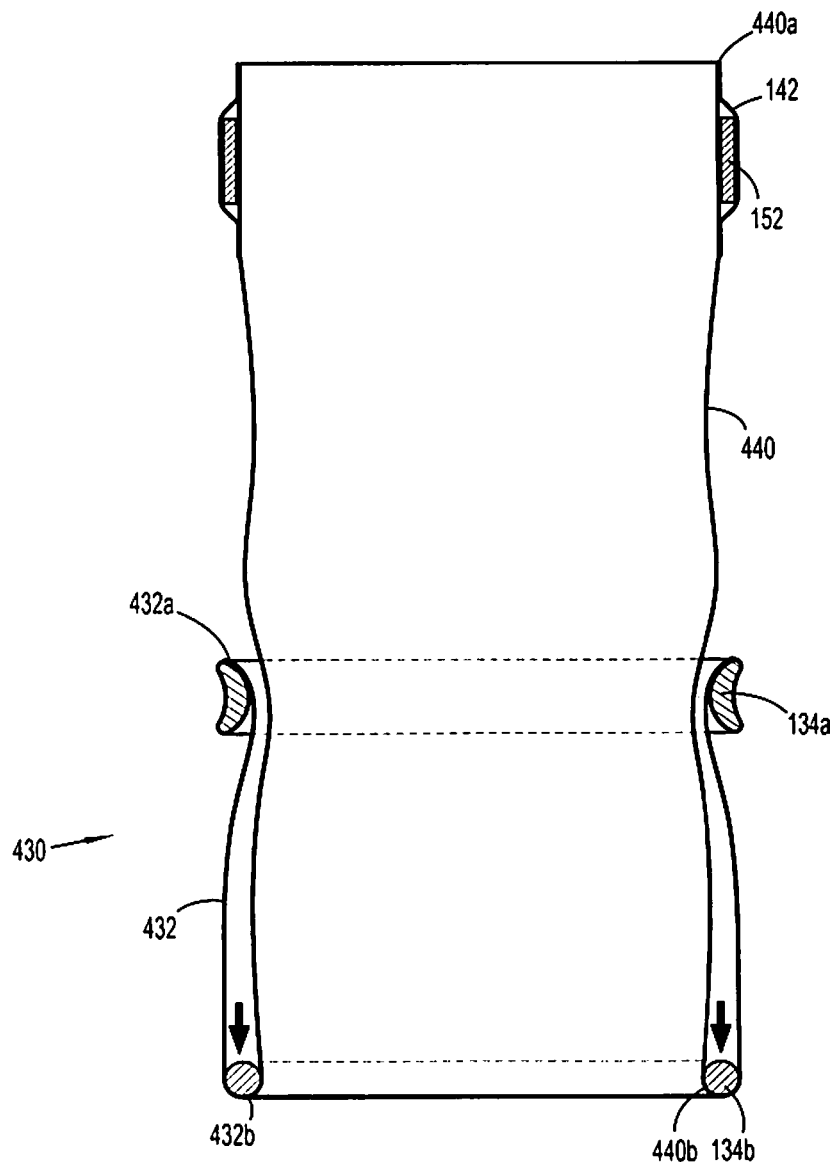
FIG. 20 is an embodiment of a sleeve with a distal end attached directly to a distal ring.

Referring for the moment to FIGS. 19-20, an alternative embodiment of a sleeve member, designated 440, is shown. Sleeve 440 is substantially similar to sleeve 140 described above, however, sleeve 440 is not formed of a continuous length of material with a membrane and looped around ring 134b. Rather, a distal end 440b of sleeve 440 is attached to a portion of membrane 432. Similarly, a distal end 432b of membrane 432 of a tissue engaging member 430 is attached directly to the ring 134b. Such attachment is accomplished by, for example, heat sealing or welding, stitching, or adhesion. Distal end 440b of sleeve 440 is defined by a portion of membrane 432, and the attachment of the distal end 440b of sleeve 440 and membrane 132 is accomplished as described above.

It is further contemplated that distal end of sleeve 440 may be attached to ring 134b in the manner described above, as shown in FIG. 20.

Turning for the moment to FIG. 8, upon receipt of the access member 110, the inner surface of sleeve 140 forms a substantially fluid-tight seal with the outer surface of access member 110. The outer surface of access member 110 and the inner surface of sleeve 140 may frictionally engage, or a lubricous surface treatment may be provided to ease insertion. The substantially fluid-tight seal between access member 110 and sleeve 140 inhibits the escape of insufflation fluids from an internal body cavity 500b below a layer of tissue 500 or the passage of fluids between the exterior and interior of the opening in tissue. As such, access members of various sizes and configurations may be inserted into a surgical site, and engagement with the sleeve 140 will ensure that an insufflated workspace is maintained in an internal body cavity below. Thus, surgical access assembly 100 allows for the use of an access member of a universal size to be used in a layer of tissue while minimizing the loss of insufflation fluid.

Sleeve 140 is configured for movement relative to the tissue engaging member 130. Once access member 110 is inserted into the sleeve 140, the coupled access member 110 and sleeve 140 may be translated distally along a portion of membrane 132 to a desired positioning within a layer of tissue 500.

Sleeve 140 may include in its outer circumference a pocket 142. Pocket 142 is a portion of sleeve 140 that protrudes from the surface of sleeve 140 and extends partially or entirely around the outer circumference of sleeve 140. Pocket 142 contains a channel formed by the outer wall of pocket 142 and the outer surface of sleeve 140. Pocket 142 may be slack relative to the rest of sleeve 140, and has at least one aperture 142a (FIG. 1) to receive and release a fastening member 150, such that a fastening member 150 may circumferentially engage and couple sleeve 140 and the access member 110 disposed therethrough.

Referring now to FIGS. 9-15, the fastening member 150 will be discussed in detail. As shown in FIG. 9, fastening member 150 includes a band 152 that has a length sufficient circumscribing an outer circumference of access member 110 and sleeve 140. Grooved surface 152a is formed of a series of ridges 152a₁ that are disposed at an angle with the surface of band 152. Fastening member 150 also includes a receiving member 154 that receives and secures band 152 in a desired position.

As shown in FIG. 10, a portion of the receiving member 154 is fixably attached to an end of the band 152. Also shown is a release 154b, which gives an operator control over the engagement of the receiving member 154 and the band 152, as will be discussed further below.

Figure 11:
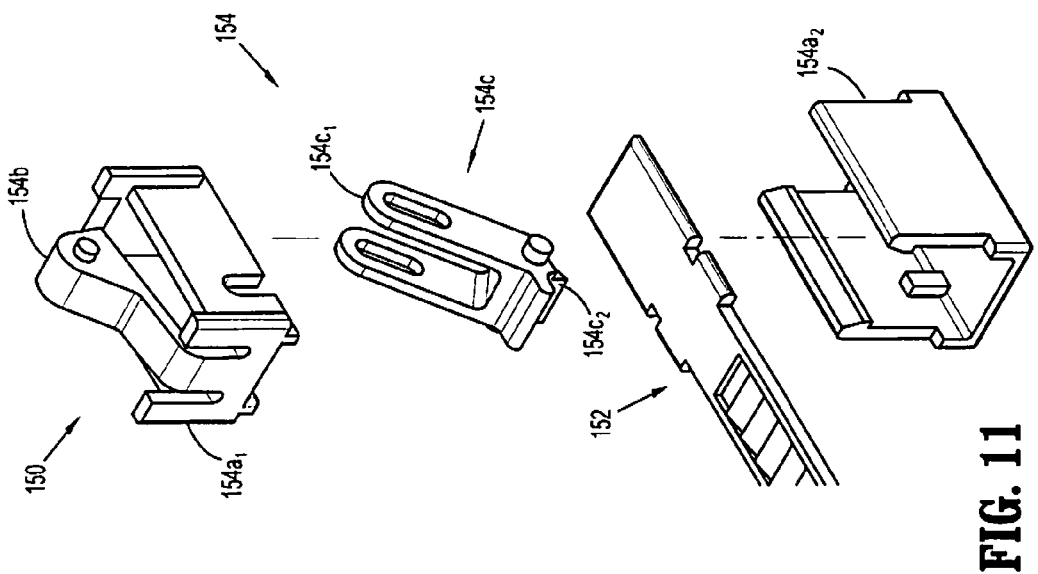
FIG. 11 is an exploded view of the receiving member and band as shown in FIG. 10.

Turning to FIG. 11, the receiving member 154 includes a top frame 154a₁, to which the release 154b is attached, and a bottom frame 154a₂. The release is coupled to a pawl 154c, which is a rigid member having a first end 154c₁ attached to the release 154b, and a second end 154c₂ that has a wedge shaped profile that engages the surface of the band 152. The first end 154c₁ of the pawl 154c may be attached to the release in a pin-and-slot configuration as shown, or by any other suitable method of attachment.

Figure 12:
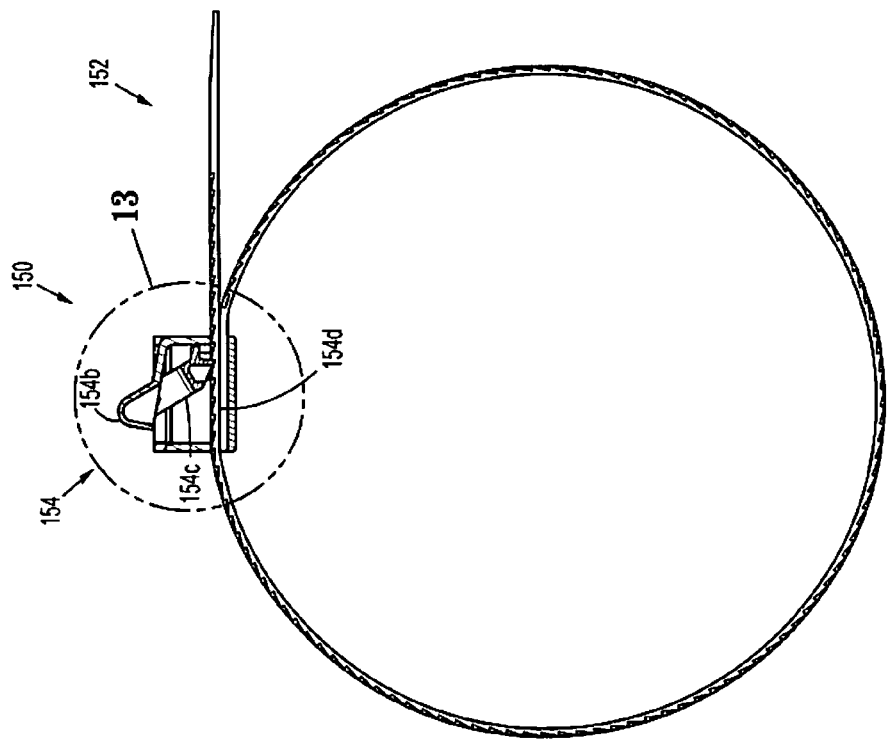
FIG. 12 is a cross-sectional view of the fastening member taken along section line 12-12 as shown in FIG. 10, with the band inserted into the receiving member.

Referring to FIG. 12, the engagement of the band 152 and the receiving member 154 is shown. The receiving member 154, when fully assembled, defines a channel 154d through which band 152 translates. The band 152 forms a loop upon insertion to the receiving member 154. As seen earlier in FIGS. 1-3, this loop circumferentially engages the access member 110 and sleeve 140 when the fastening member 150 is disposed in the pocket 154.

Figure 13:
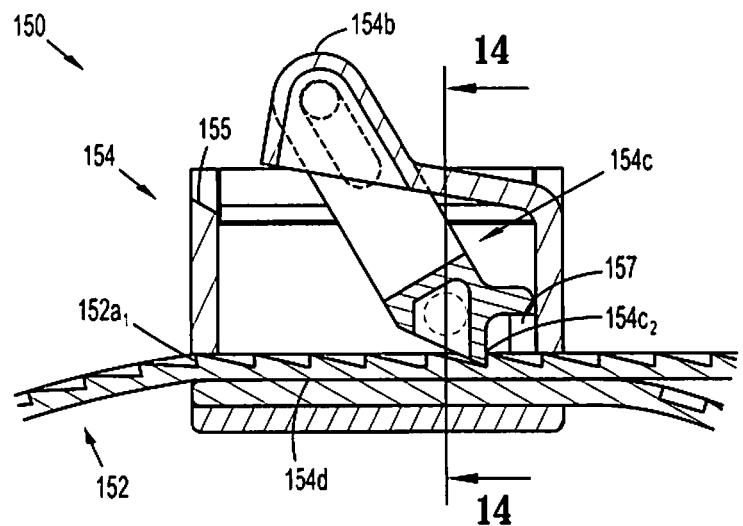
FIG. 13 is an enlarged detail view of the cross-section of the receiving member shown in FIG. 12.
Figure 14:
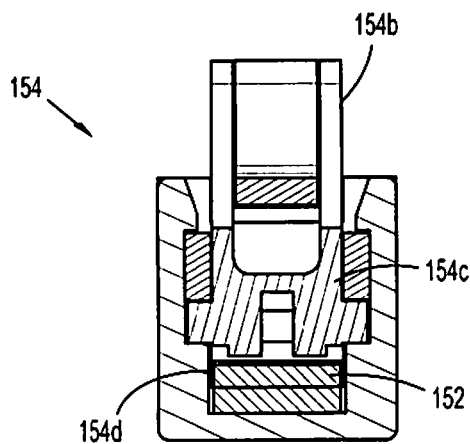
FIG. 14 is a cross-sectional view of the receiving member as shown in FIG. 13 taken along section line 14-14.

Turning to FIG. 13, grooved surface 152a is defined by a series of ledges and spaces formed by the angled ridges 152a₁. The angle at which pawl 152c is disposed causes second end 154c₂ of the pawl 152c to slide over the ridges angled ridges 152a₁ as the band 152 is translated through the channel 154d. Additionally, receiving member 154 includes a first or forward stop 155 and a second or back stop 157. First stop 155 limits the travel of pawl 154c in a first direction such that second end 154c₂ of pawl 154c seats in the notch of band 152. Second stop 157 limits the travel of pawl 154c in a second, opposite direction.

If band 152 is subject to forces that tend to translate the band 152 out of the receiving member 154, pawl 154c interferes with the ridges 152a₁ as it is biased toward a space in between the ridges 152a₁. The pawl 154c thus inhibits motion of the band 152 out of the receiving member 154. Thus, fastening member 150 may be secured and tightened around the access member 110 and the sleeve 140, but the band 152 may not slip out of the channel 154d without the intervention of an operator.

As the ridges 152a₁ are disposed at an angle, the pawl 154c slides over each ridge 152a, to the apex of each ridge 152a₁, and then is forced into the space between ridges 152a₁ under a biasing force. This engagement of the pawl 154c and the grooved surface 152a (FIG. 9) is continuously repeated for the length of band 152a. As shown in the front view through the channel 154d of FIG. 14, the band 152 is free to translate through the channel 154d without interference.

Figure 15:
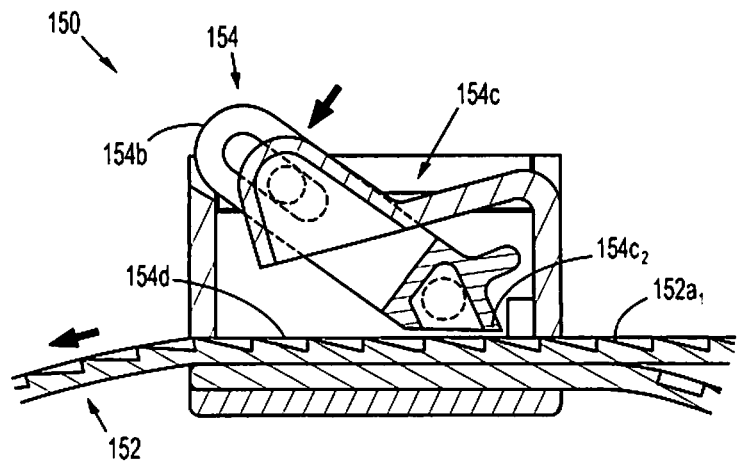
FIG. 15 is a side cross-sectional view of the receiving member as shown in FIG. 13, with the band being disengaged from the receiving member.

Referring to FIG. 15, disengagement of the band 152 from the receiving member 154 is shown. In the event that it is desired that the fastening member 150 be loosened, the release 154b may be engaged by the operator. As the release 154b is forced away from the channel 154d by the operator, the biasing force on the pawl 154c is overcome and the pawl 154c is moved away from the band 152 as it is disposed in the channel 154d. Without interference from the pawl 154c, the band 152 is free to translate into or out of the receiving member 154.

Figure 17:
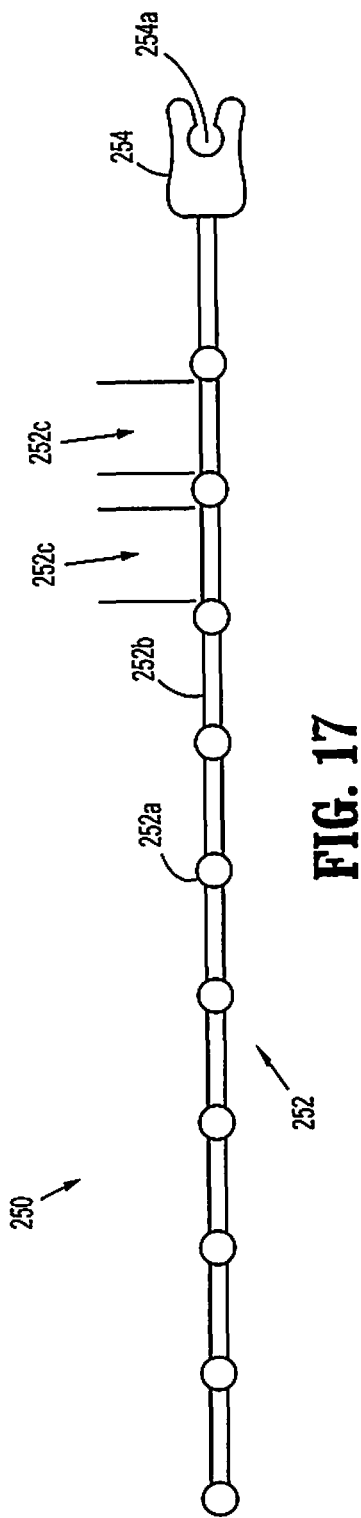
FIG. 17 is an embodiment of a fastening member having spaced protrusions along its length.

Referring for the moment to FIG. 17, a fastening member 250 is shown. Fastening member 250 includes a band 252 that has a length sufficient for circumscribing an outer circumference of access member 110 and sleeve 140. Like fastening member 150 described above, fastening member 250 is to be disposed in the pocket 142 around the circumference of sleeve 140.

Band 252 includes spaced protrusions 252a. Protrusions 252a may be beads, as shown, or may any other desirable shape. Protrusions 252a are interconnected by a connecting member 252b, and are disposed at points along the band 252 that have spaces 252c between them. Protrusions 252a may be spaced at regular intervals with spaces 252c of equal length, or may be disposed at varied intervals as desired.

Fastening member 250 also includes a receiving member 254 having an aperture 254a that receives band 252. Aperture 254a may securely engage a protrusion 252a, or may be configured to engage a connecting member 252b and space 252c between protrusions 252a.

Figure 18:
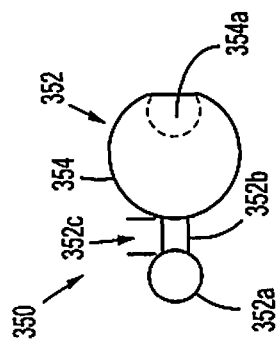
FIG. 18 is an embodiment of a fastening member having separable members.

Turning to FIG. 18, in another embodiment, a fastening member 350 is formed of separable members 352 having at least a first protrusion 352a and a connecting member 352b disposed through a space 352c between protrusions 352a. A receiving protrusion 354 has an aperture 354a to securely engage protrusion 352a. Thus, a successive first protrusion 352a in a series of separable members may be inserted into aperture 354a, forming fastening member 350. As with fastening members 150 and 250 as described above, fastening member 350 may be disposed in the pocket 142 around the circumference of access member 110 and sleeve 140.

Referring back to FIG. 1, the tissue engaging member 130 and sleeve 140 are shown fully disassembled and unrolled. The tissue engaging member 140 is inverted before insertion into a layer of tissue 500, with the distal end 132b of the membrane 132 located proximally of the proximal end 132b of the membrane 132. The fastening member 150 may be disposed through the pocket 142, or may be inserted later. The ring 134b to be located at the distal end 132b of the membrane 132 is slid over the proximal end 140a of the sleeve 140 to a desired length where the distal end 132b of the membrane 132 and the distal end 140b of the sleeve 140 will be formed.

Figure 2:
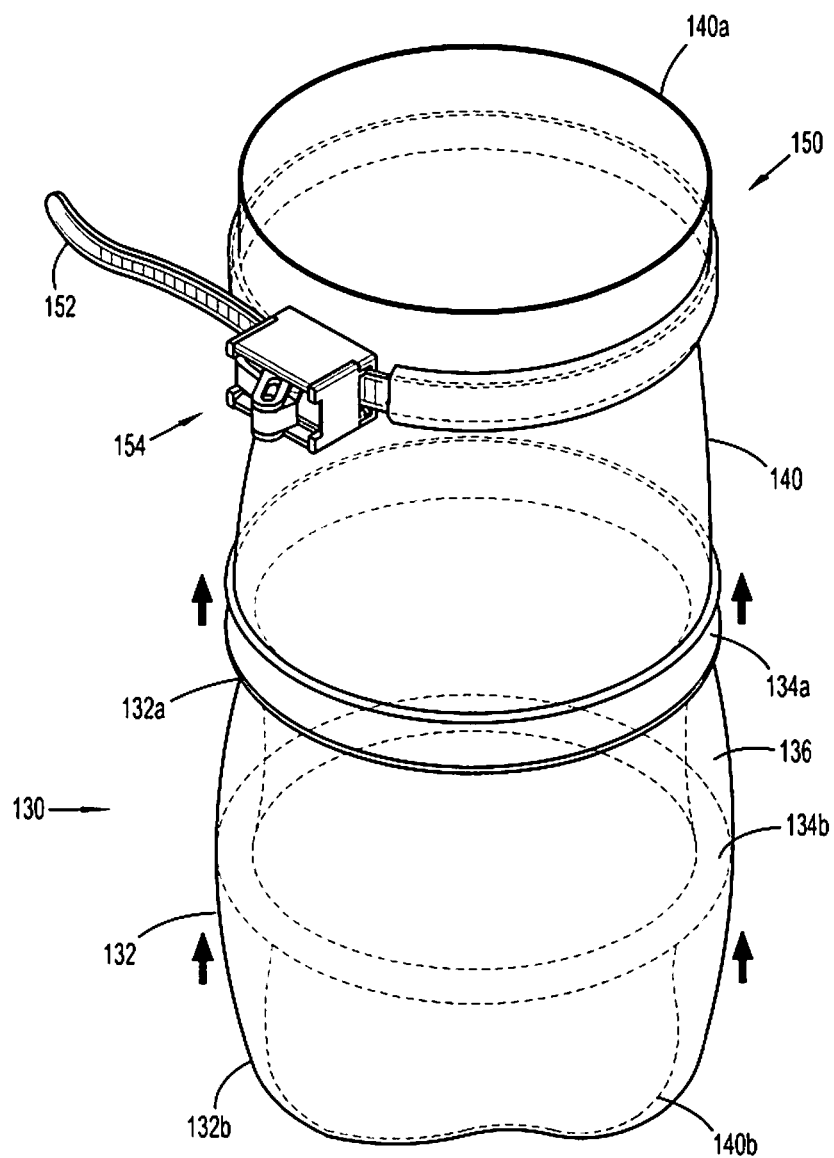
FIG. 2 is a side perspective view of the surgical access assembly of FIG. 1 without the access member as it appears as the tissue engaging member and sleeve are formed about a pair of rings.
Figure 3:
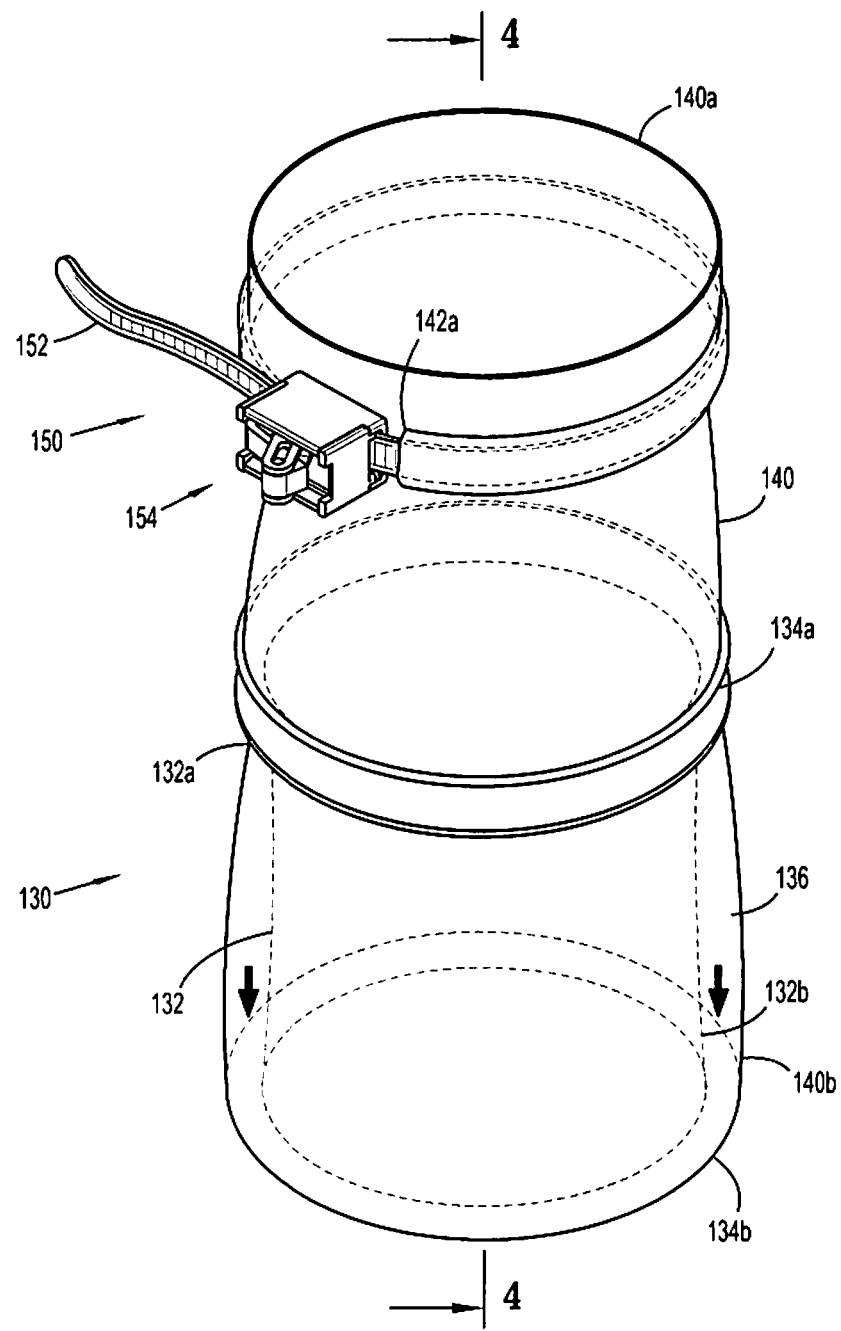
FIG. 3 is a side perspective view of the surgical access assembly as shown in FIG. 2 as it appears before insertion into a layer of tissue.

Turning now to FIG. 2, the tissue engaging member 130 and sleeve 140 are shown as they are prepared to be inserted into a layer of tissue 500 (FIG. 3). The proximal end 132a of membrane 132, attached to ring 134a, is raised proximally of and outside the ring 134a. A cuff 136 is formed between the proximal ring 134a and the point at which the membrane 132 is inverted. Distal ring 134b is disposed at a point along the cuff 136.

Referring to FIG. 3, the ring 134b is slid distally through the cuff 136 and defines the distal end 132b of the membrane 132, and the distal end 140b of the sleeve 140, at its final resting position. With the ring 134b in place, the tissue engaging member 130 and the sleeve 140 are fully defined as they are to be disposed in a layer of tissue 500.

Turning now to FIG. 5, the distal ring 134b is compressed and deformed so as to fit through a layer of tissue 500. As such, distal ring 134b is formed of a material that is resilient, but flexible enough so as to be substantially deformed upon insertion into a layer of tissue 500, such as rubber or foam. When the distal ring 134b has passed through a layer of tissue 500, the distal ring will revert to its original annular shape. Sleeve 140 and proximal ring 134a remain disposed proximally above the layer of tissue 500.

Figure 6:
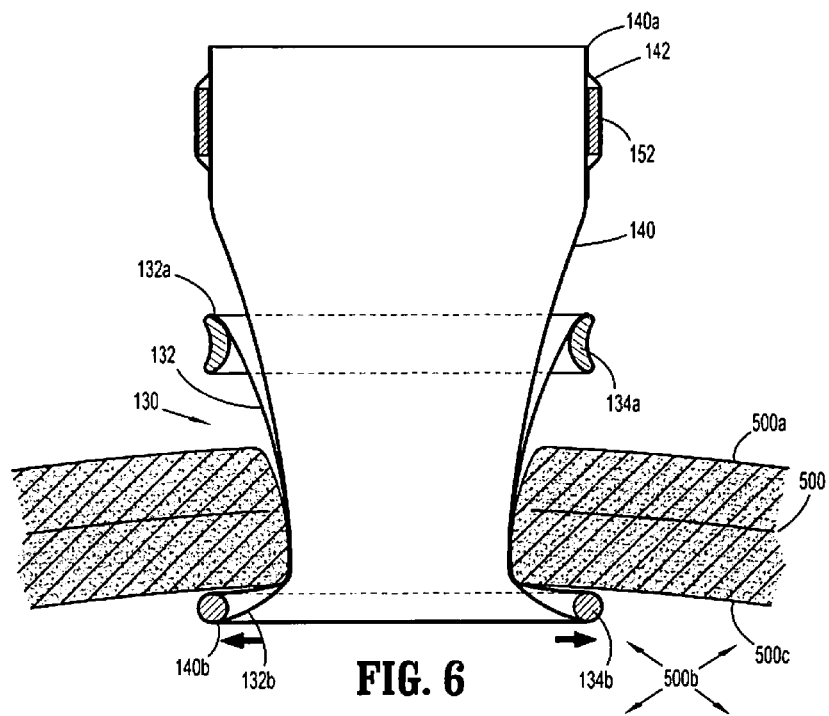
FIG. 6 is a cross-sectional view of the surgical access assembly as shown in FIG. 5 as an excess length of the sleeve is pulled away from the layer of tissue.

Referring to FIG. 6, the tissue engaging member 130 and sleeve 140 are shown disposed in the layer of tissue 500. An operator adjusts the tissue engaging member 130 and the sleeve 140 to adapt to the particular needs of the surgical site. As the proximal end 132a of the membrane 132 is translated proximally above the layer of tissue 500, material from the sleeve 140 slides under the ring 134b. Thus, the operator can change the length of the sleeve 140.

Figure 7:
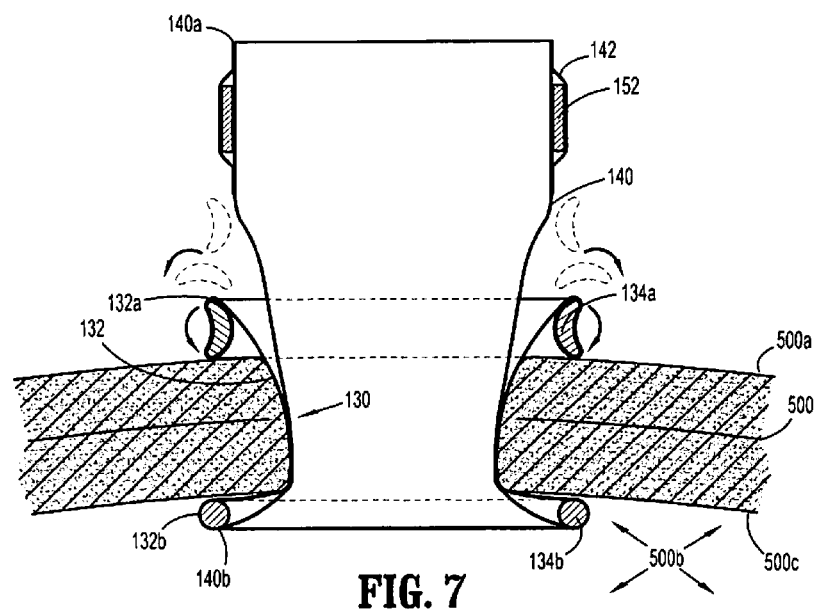
FIG. 7 is a side profile view of the surgical access assembly as shown in FIG. 6, as the excess length is rolled about a proximal ring by an operator.

Turning now to FIG. 7, the ring 134a is shown as it is rolled by an operator. Excess membrane 132 and sleeve 140 material is rolled over the ring 134a, and the ring 134a is rolled toward the body surface 500a. As compared to a ring with a circular profile, the arcuate or kidney bean shaped profile of the ring 134a inhibits unrolling of the material disposed over the ring 134a by providing a flattened edge disposed over body surface 500a that counteracts moments about the ring 134a.

In the alternative embodiment of sleeve 440 described above, rolling the ring 134a causes the length of tissue engaging member 130 to shorten, but does not change the length of sleeve 440.

Figure 16:
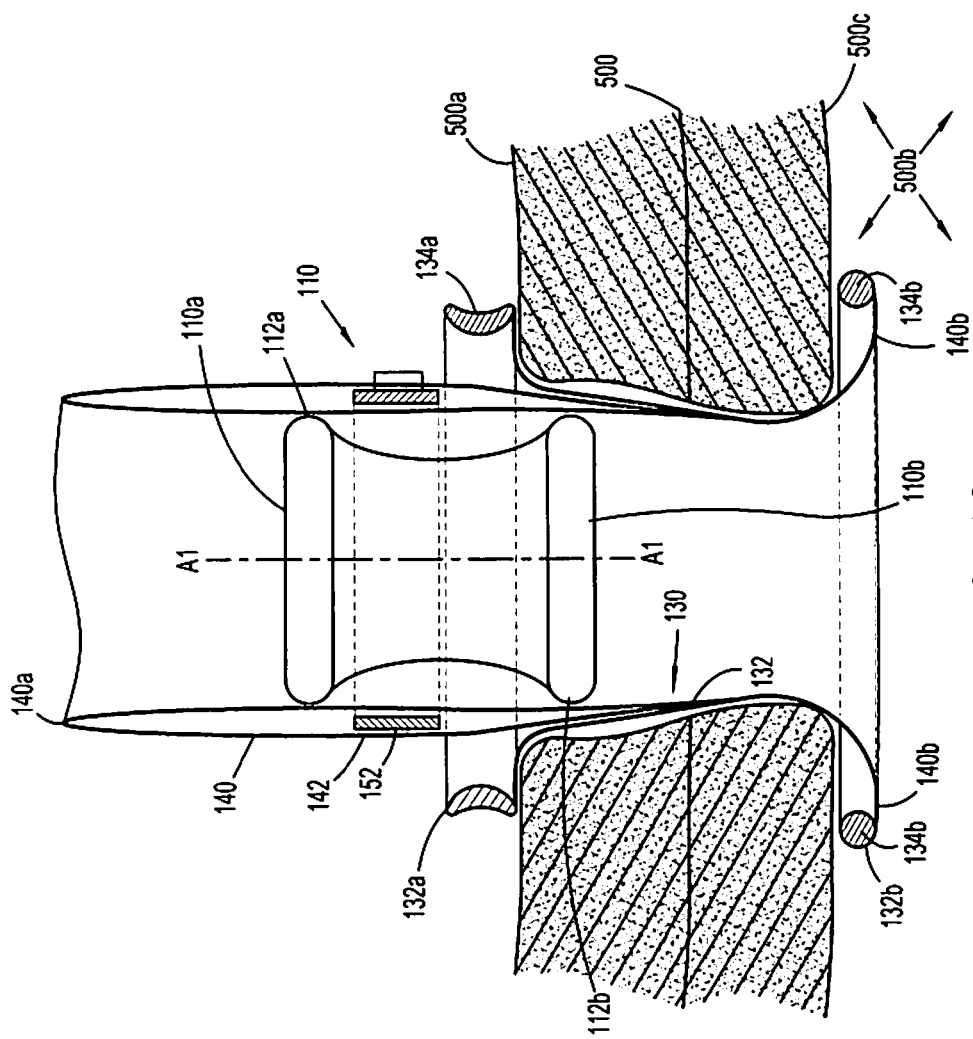
FIG. 16 is a cross-sectional view of the surgical access assembly as shown in FIG. 8, without a surgical instrument, with an excess length of the sleeve prepared to be removed.

Referring for the moment to FIG. 16, it is further contemplated that an excess length of sleeve 140 extending proximally above the access member 110 may be removed by an operator. Constraints imposed by the nature of the surgical site or the nature of the procedure may make it preferable to excise an excess length of sleeve 140 rather than taking up slack by rolling the ring 134a as described above.

Turning to FIG. 8, with the tissue engaging member 130 disposed in a layer of tissue 500, the access member 110 is inserted into sleeve 140. To aid in maintaining the substantially fluid-tight seal formed between the access member 110 and the sleeve 140, the band 152 of the fastening member 150 is inserted into the receiving member 154 (FIG. 9). The engagement of the grooved surface 152a (FIG. 9) with the receiving member 154 allows an operator control over the compressive force exerted around the access member 110 and sleeve 140. Fastening member 150 may be tightened to a desired degree, and ensures that the sleeve 140 will not move independently of the access member 110.

The access member 110, disposed within the sleeve 140, may then be inserted into the layer of tissue 500. As the access member 110 and sleeve 140 are inserted distally along the longitudinal axis, the outer surface of sleeve 140 is in contact with the membrane 132. Sufficient length of the sleeve 140 must be present distally of the access member 110 such that the sleeve 140 is not rolled or slid away from the access member 110 as the access member 110 and the sleeve 140 are translated distally into a layer of tissue. Sleeve 140 and membrane 132 may frictionally engage, or may be provided with a lubricous surface treatment so as to ease insertion into the layer of tissue 500.

With the surgical access assembly 100 secured in the layer of tissue 500, one or more surgical instruments 600 can be inserted through the lumens 120 of the access member 110. Lumens 120 provide an unobstructed path from points proximal of the surgical access assembly 100 to an internal body cavity 500b below the layer of tissue 500. Thus, an operator can control a surgical instrument 600 to perform minimally invasive procedures in an internal body cavity 500b.

Alternatively, the proximal ring 134a may be further rolled such that the sleeve 140 is shortened until the access member 110 and sleeve 140 are disposed in the layer of tissue 500. With the access member 110 secured to the layer of tissue 500 with the flanges 112a,b at the proximal 110a and distal ends 110b of the access member 110, additional rolling of the ring 134a may retract a layer of tissue 500 and widen a surgical site.

In this way, access members of various sizes may be utilized through an incision in tissue or naturally occurring orifice which has a larger diameter than the surgical access member. It is contemplated that the surgical access member may be inserted before, during or after the sleeve has already been positioned within an incision. Also, the size of the openings through any of the sleeves may enable a specimen to be removed and/or passed through the incision (e.g., the permanent removal of diseased internal anatomy and/or the temporary exteriorization of portions of the colon to be manipulated outside of the body before being returned to inside the body) without the need to remove the sleeve, thereby providing, via the sleeve, a protective layer for the incision against, e.g., contamination via cancer cell seeding or the like. Still further, with the sleeve, the user may selectively increase the size of the incision during the course of the surgical procedure (e.g., a surgeon may make an initial relatively small incision—such that the surgical access port is maintained in the incision without the sleeve being used—and may later, if the surgeon decides that doing so is warranted, make a larger incision—such that the surgical access member is maintained in the incision with the sleeve being present. This flexibility may enable a surgeon to minimize the size of the incision made during the surgical procedure, as the surgeon may wait to make a larger incision until after he or she has determined, using the initially smaller incision, to enlarge the incision based on his or her observations. It also enables the surgeon to utilize the same surgical access member regardless of the size of the incision and regardless of whether the surgeon elects to make an initially small incision or to make an initially larger incision, thereby eliminating the need for different sized surgical access members. It should be noted that these above-described benefits are applicable to all of the embodiments set forth herein.

What is claimed is:

1. A surgical access assembly comprising:
    a proximal ring positionable against an outer surface of body tissue;
    a distal ring positionable against an inner surface of body tissue;
    a membrane having a proximal end and a distal end defining a passage therethrough, the distal end of the membrane coupled to the distal ring and the proximal end of the membrane coupled to the proximal ring, a length of the membrane being selectively adjustable;
    a sleeve having a proximal end and a distal end defining a channel therethrough, the distal end of the sleeve coupled to the distal ring and the proximal end positionable proximally of the proximal ring, the channel of the sleeve located in the passage of the membrane; and
    an access member having proximal and distal ends, the access member positionable in the channel of the sleeve, the access member securable to the sleeve.

2. The surgical access assembly of claim 1, wherein the access member includes a least one lumen extending therethrough.

3. The surgical access assembly of claim 1, further comprising a fastening member for securing the access member in the channel of the sleeve.

4. The surgical access assembly of claim 1, wherein the access member, the sleeve, and the membrane form a fluid-tight seal between the outer surface of body tissue and the inner surface of body tissue.

5. The surgical access assembly of claim 3, wherein the fastening member is disposed in a pocket located on a surface of the sleeve.

6. The surgical access assembly of claim 5, wherein the fastening member is configured to be tightened to secure a position of the access member relative to the pocket.

7. The surgical access assembly of claim 5, wherein the pocket has at least one opening for receiving an end of the fastening member.

8. The surgical access assembly of claim 1, wherein the proximal ring is configured for repeated eversion to adjust a length of the sleeve.

9. The surgical access assembly of claim 8, wherein the access member is positionally fixed relative to the sleeve such that repeated eversion of the proximal ring moves the access member relative to the distal ring.

10. The surgical access assembly of claim 1, wherein repeated eversion of the proximal ring adjusts a length of the sleeve and the length of the membrane.

11. The surgical access assembly of claim 1, wherein rolling the proximal ring adjusts the length of the membrane so as to provide a retraction force.

12. The surgical access assembly of claim 6, wherein the fastening member includes a grooved surface and a receiving member that securely engages the grooved surface.

13. The surgical access assembly of claim 6, wherein the fastening member further includes angled ridges and a pawl, the pawl attached to a release member.

14. The surgical access assembly of claim 1, wherein the access member is securable against an inner surface of the sleeve.

15. The surgical access assembly of claim 1, wherein the distal end of the access member is positionable distally of the proximal ring.

* * * * *